United States Patent [19]

Randvere et al.

[11] 4,212,971
[45] Jul. 15, 1980

[54] PROCESS FOR PREPARING METHYLENE BLUE

[75] Inventors: Fredrik V. Randvere, Manville; Leroy M. Konzelman, Livingston, both of N.J.

[73] Assignee: American Cyanamid Company, Stamford, Conn.

[21] Appl. No.: 18,710

[22] Filed: Mar. 8, 1979

[51] Int. Cl.$^2$ ............................................ C07D 279/18
[52] U.S. Cl. ...................................................... 544/37
[58] Field of Search ............................................ 544/37

[56] References Cited

U.S. PATENT DOCUMENTS 2,069,670   2/1937   Hoffmann ...................... 544/37 OR

OTHER PUBLICATIONS

Venkataraman, The Chemistry of Synthetic Dyes, vol. II, frontispage and pp. 792–793, Academic Press Inc. NY (1952).
Tomioka, Chem. Abstracts, vol. II, pp. 1305 to 1306.
Lubs, The Chemistry of Synthetic Dyes and Pigments, frontispage and pp. 266 to 269, Reinhold Publishing Corp. (NY) (1955).
Highet et al., J. Am. Chem. Soc., vol. 77, pp. 4399 to 4401 (1955).
Barakat et al., Chem. Abstracts, vol. 51, col. 4998 (1957).
Kendall, General Chemistry, frontispage and 647–652, D-Appleton-Century Co., 1936.

*Primary Examiner*—John D. Randolph
*Attorney, Agent, or Firm*—Bruce F. Jacobs

[57] ABSTRACT

Methylene Blue and the zinc chloride double salt thereof are prepared by using manganese dioxide as the oxidizing agent in the substantial absence of toxic dichromates.

6 Claims, No Drawings

PROCESS FOR PREPARING METHYLENE BLUE

This invention relates to processes for preparing Methylene Blue and the zinc chloride double salt thereof.

In accordance with the present invention, improved processes are provided for the manufacture of Methylene Blue represented by formula (I):

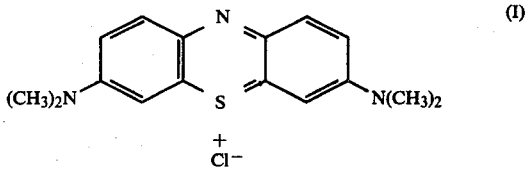

and the zinc chloride double salt thereof, represented by formula (II):

2 (I) . ZnCl$_2$ . H$_2$O      (II)

which has the Color Index No. 52015.

These processes entail the conversion of N,N-dimethyl-p-phenylenediamine, by treatment with manganese dioxide and sodium thiosulfate in the presence of an acid, to form 2-amino-5-dimethylaminophenyl thiosulfonic acid, represented by formula (III):

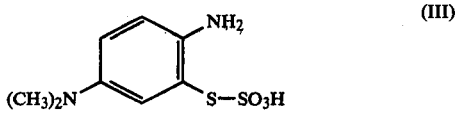

conversion of the latter compound with manganese dioxide and N,N-dimethylaniline to the indamine-thiosulfonic acid represented by formula (IV):

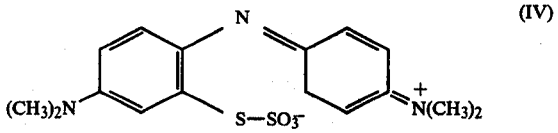

and conversion of the latter by cyclization and oxidation with manganese dioxide and copper sulfate to Methylene Blue, which may be optionally isolated as the zinc chloride double salt.

Since the discovery of Methylene Blue by Caro in 1876, many approaches to its preparation have been investigated. Although a large volume of scientific work has been disclosed, see Colour Index 52015, the only method suitable for the commercial manufacture of Methylene Blue involves the formation of (III) and (IV), and the oxidation and cyclization of (IV) utilizing a dichromate, a mixture of a dichromate and copper sulfate, or a mixture of a dichromate and manganese dioxide.

Dichromates are toxic. The use of the dichromates creates environmental problems, involving the disposal of large volumes of sludge containing chromium. Hence, there is need for a process of making methylene Blue that eliminates the use of the dichromate salt.

Accordingly, the present invention provides a process for the preparation of Methylene Blue, and the zinc chloride double salt thereof, without the use of toxic dichromates.

The processes of the present invention offer the following advantages:

1. The Methylene Blue, or the zinc chloride double salt thereof, is obtained in high quality, and excellent yields.
2. Since manganese is not environmentally toxic, there are not problems with pollution by the effluent, and the disposal of the oxidation sludge.
3. The volume of oxidation sludge is considerably reduced, thereby reducing handling cost and allowing for an increase in production.

Methylene Blue may be prepared by (a) reacting a mixture of N,N-dimethyl-p-phenylenediamine, an inorganic oxidizing agent, sodium thiosulfate, and sulfuric or hydrochloric acid, in water to form a solution of 2-amino-5-dimethylaminophenylthiosulfonic acid; (b) adding to the reaction mixture N,N-dimethylaniline hydrochloride, additional oxidizing agent, and additional acid to form a solution of the indamine-thiosulfonic acid represented by formula (IV) above; (c) treating the reaction mixture with a mixture of copper sulfate and said oxidizing agent and heating the reaction mixture until the formation of Methylene Blue is completed. The present invention entails the use of manganese dioxide as the oxidizing agent in the substantial absence of dichromate compounds. Furthermore, when the copper sulfate is used in at least about 0.017 mole per mole of N,N-dimethyl-p-phenylenediamine an increased yield of Methylene Blue is produced.

More specifically, Methylene Blue may be prepared by treating one molecular proportion of N,N-dimethyl-p-phenylenediamine with about 0.8–5.0 moles of manganese dioxide, preferably about 0.8–1.5 moles, in water at about $-15°$ C. to 98° C., preferably about 0° C. to 5° C., in the presence of about 0.7–2.0 moles of sodium thiosulfate, preferably about 0.8–1.3 moles, and about 0.5–6 molecular equivalents of sulfuric acid or hydrochloric acid, preferably about 1–3 molecular equivalents of sulfuric acid, to form a slurry containing the compound of formula (III). The resulting reaction mixture is then treated with about 0.7–1.5 moles of N,N-dimethylaniline hydrochloride, preferably about 0.8–1.0 mole, in the presence of about 1.5–4.5 moles of manganese dioxide, preferably about 2.0–3.0 moles, and about 2–20 molecular equivalents of sulfuric acid or hydrochloric acid, preferably about 4–6 molecular equivalents of sulfuric acid, at about $-15°$ C. to 98° C., preferably about 0° C. to 20° C., to form a slurry containing the compound of formula (IV). The compound of formula (IV) is then oxidized and cyclized by adding to the reaction mixture at least about 0.017 moles of copper sulfate, (though more may be used), preferably about 0.1–0.3 mole of copper sulfate pentahydrate, and about 0.5–1.5 moles of manganese dioxide, preferably about 0.7–1.2 moles, heating the reaction mixture at a pH of about 2–7, preferably about 3–6, to about 40° C. to 100° C., preferably about 70° C. to 98° C., and maintaining it thereat until the formation of Methylene Blue is completed, as determined by conventional spot tests known in the art. Methylene Blue may then be recovered by conventional means. A particularly suitable method is to clarify the reaction mixture at about 50° C. to 100° C., preferably about 80° C. to 100° C., to remove insolubles, and then adjust the pH of the mother liquor to about 5–6, preferably about 5.2–5.5, by adding an alkalizing agent, preferably caustic soda, thereto. Preferably, any insoluble material recovered is washed with hot water and the wash liquor is combined with the mother liquor before adjusting the pH to about 5-6. After the pH is adjusted, the reaction mixture may be clarified again, if necessary, to remove additional insolubles. The clarified solution is then cooled to about 0° C. to 10° C., preferably about 5° C. to 8° C., and stirred thereat until precipitation of Methylene Blue is completed. The product is then recovered, washed with cold water, and dried by conventional means.

The invention also provides a process for preparing the zinc chloride double salt of Methylene Blue of formula (II) by carrying out the above-described process, adjusting the pH of the mother liquor, or the mother liquor plus wash liquor, to about 2-3, preferably to about 2.5 with hydrochloric acid, adding thereto about 0.5-1.0 mole of zinc chloride, preferably about 0.7-0.9 mole, per mole of N,N-dimethyl-p-phenylenediamine used, and recovering the zinc salt by conventional means. Preferably, after adding the zinc chloride, a water-soluble salt such as sodium sulfate, sodium chloride, and the like, is added to the solution in order to salt out the zinc chloride double salt.

In the examples which follow, the manganese dioxide used is 85.2% real, the sodium thiosulfate is 27.4 volume percent in water, the sulfuric acid is 53.95 volume percent in water and the sodium hydroxide is 50% by weight in water. Unless otherwise specified, parts and percentages are on a weight basis.

EXAMPLE 1

Preparation of Methylene Blue

A solution (400 mls) of N,N-dimethyl-p-phenylenediamine 0.05 mole), is diluted with ice water (3° C.) to a volume of 632 mls, charged to a reaction vessel and cooled to 0° C. Manganese dioxide (8.6 grams; 0.084 mole), sodium thiosulfate (50.5 mls, or 13.85 grams real; 0.088 mole) and sulfuric acid (6.86 mls, or 3.7 grams real; 0.038 mole) are added thereto while stirring at 3°-7° C. The reaction mixture is stirred at 5°-8° C. for 44 minutes, and sodium hydroxide (1.25 grams; 0.015 mole) is added thereto to adjust the pH to about 5.

A solution (19.35 grams) of N,N-dimethylaniline hydrochloride (10.72 grams; 0.068 mole) in water is added thereto and the reaction mixture is stirred rapidly at 7°-9° C. for one minute. Manganese dioxide (20.8 grams; 0.204 mole) is added to the reaction mixture at 7°-12° C. over about a minute, followed by the addition of sulfuric acid (35.1 mls, or 18.95 grams real; 0.19 mole) at 8°-12° C. over a period of 20 minutes. The resulting mixture is stirred at 10°-12° C. for one hour, and sodium hydroxide (12.5 grams; 0.15 mole) is added thereto to adjust the pH to 4.2.

Copper sulfate pentahydrate (3.4 grams; 0.014 mole) and manganese dioxide (7.7 grams; 0.075 mole) are then added to the reaction mixture. The mixture is then stirred rapidly and heated to 90° C. over a period of 13 minutes, maintained at 90° C. for 30 minutes, and clarified to remove insolubles. The insolubles are washed with 100 mls of water at 90° C. and the wash liquor is combined with the filtrate.

The combined filtrate and wash liquor is cooled to 60° C. and sodium sulfate (7.5 grams), sodium carbonate (0.5 gram to adjust the pH to about 5), and a filter aid (1.25 grams of Hyflo ® Super-Cel, Johns-Manville Corporation) are added thereto. The resulting mixture is clarified by filtration at 60° C. and the filter cake is washed with 50 mls of hot water (90° C.). The combined filtrate and wash liquor is cooled to 5° C. and stirred thereat for 3 hours. The precipitate is separated by filtration, washed with 40 mls of cold water (4° C.), sucked dry, and dried at 60° C. There is obtained 15.9-17.0 grams of Methylene Blue of excellent color value.

EXAMPLE 2

Preparation of Zinc Chloride Double Salt of Methylene Blue

The procedure of Example 1 is followed except that the combined filtrate and wash liquor (70° C.) from the first clarification is adjusted to a pH of 2.5 by adding hydrochloric acid thereto, sodium chloride (50 grams) and 50% aqueous zinc chloride (19.6 grams; 0.072 mole) are added at 70° C., the reaction mixture is stirred for 12 minutes, and the insoluble precipitate is separated by filtration. After drying the precipitate, there is obtained 20.0 grams of the zinc chloride double salt of Methylene Blue of excellent color value.

In the manner described in Example 1 and above, substituting hydrochloric acid (10.46 grams of 20° HCl; 0.085 mole) and (47.1 grams of 20° HCl; 0.387 mole) for the sulfuric acid in the first and second oxidation steps, respectively, of Example 1, there is obtained 17.1 grams of the zinc chloride double salt of Methylene Blue.

EXAMPLE 3

The procedure of Example 1 is followed except that the third oxidation step is carried out in the presence of a filter aid (4.0 grams of Hyflo ® Super-Cel) and the dye is precipitated as the zinc chloride double salt in the manner of Example 2. After drying, there is obtained 20.4 grams of the zinc chloride double salt of Methylene Blue of excellent color value.

EXAMPLES 4-7

Preparations of Methylene Blue with Different Amounts of Copper Sulfate

EXAMPLE 4

A solution (391 mls) of N,N-dimethyl-p-phenylenediamine (11.0 grams; 0.081 mole), containing sulfuric acid (4.69 grams; 0.048 mole), is diluted with ice water (3° C.) to a volume of 632 mls, charged to a reaction vessel and cooled to 0° C. Manganese dioxide (8.6 grams; 0.084 mole), sodium thiosulfate (50.5 mls, or 13.85 grams real; 0.088 mole) and sulfuric acid (7.3 mls, or 3.94 grams real; 0.040 mole) are added thereto while stirring at 3°-7° C. The reaction mixture is stirred at 5°-8° C. for 35 minutes, and sodium hydroxide (1.25 grams; 0.015 mole) is added thereto to adjust the pH to about 5.3.

A solution (19.94 grams) of N,N-dimethylaniline hydrochloride (10.72 grams; 0.068 mole) in water is added thereto and the reaction mixture is stirred rapidly at 7°-10° C. for 2 minutes. Manganese dioxide (20.8 grams; 0.204 mole) is added to the reaction mixture at 7°-12° C. over about one minute, followed by the addition of sulfuric acid (35.1 mls, or 18.95 grams real; 0.19 mole) at 8°-12° C. over a period of 20 minutes. The resulting mixture is stirred at 10°-12° C. for one hour, and sodium hydroxide (12.5 grams; 0.15 mole) is added thereto to adjust the pH to 4.2.

Copper sulfate pentahydrate (3.4 grams; 0.014 mole) and manganese dioxide (7.7 grams; 0.075 mole) are added to the reaction mixture. The reaction mixture is then stirred rapidly and heated to 90° C. over a period of 22 minutes then heated to 100° C. and held thereat for 35 minutes. The reaction mixture is clarified at 90°-100° C. to remove insolubles which are then washed with 150 mls of water at 90° C.

The wash liquor is then combined with the clarified mother liquor, cooled to 60° C. and processed as described in Example 1. There is obtained 14.3 grams of Methylene Blue of excellent color value.

EXAMPLE 5

The procedure of Example 4 is followed in every detail except that no copper sulfate pentahydrate is added to the reaction mixture. There is obtained only 1.3 grams of Methylene Blue, which represents 9.1% of the amount obtained in Example 4.

EXAMPLE 6

The procedure of Example 4 is followed in every detail except that 0.34 gram (0.0014 mole) of copper sulfate pentahydrate is added to the reaction mixture. This corresponds to 0.017 moles per mole of N,N-dimethyl-p-phenylene diamine. There is obtained 9.1 grams of Methylene Blue, which represents 63.6% of the amount obtained in Example 4.

EXAMPLE 7

The procedure of Example 4 is followed in every detail except that 1.7 grams (0.007 mole) of copper sulfate pentahydrate is added to the reaction mixture. There is obtained 13.7 grams of Methylene Blue, which represents 95.8% of the amount obtained in Example 4.

We claim:

1. In a process for preparing Methylene Blue by (a) reacting a mixture of N,N-dimethyl-p-phenylenediamine, an inorganic oxidizing agent, sodium thiosulfate, and sulfuric acid, or hydrochloric acid, in water to form a solution of 2-amino-5-dimethylaminophenyl thiosulfonic acid, (b) adding to the reaction mixture N,N-dimethylaniline hydrochloride, additional oxidizing agent, and sulfuric acid, or hydrochloric acid, to form a solution containing a compound represented by the formula:

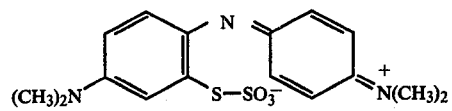

(c) treating the reaction mixture with a mixture of copper sulfate and said oxidizing agent and heating the reaction mixture until the formation of Methylene Blue is completed, and recovering Methylene Blue therefrom, the improvement which comprises: using about 0.8 to 5.0 mole of manganese dioxide as the oxidizing agent in the substantial absence of a dichromate and in the presence of at least 0.017 mole of copper sulfate per mole of N,N-dimethyl-p-phenylenediamine initially charged.

2. The process according to claim 1 wherein the Methylene Blue is recovered by (i) clarifying the reaction mixture and adjusting the pH of the resulting mother liquor to about 5-6 and (ii) cooling the mother liquor.

3. The process according to claim 2 wherein step (a) is carried out at 0°-15° C., step (b) is carried out at 0°-20° C., in step (c) the reaction mixture is heated at 70°-98° C., and in the recovery (ii) the mother liquor is cooled to about 5°-10° C. before separating the Methylene Blue.

4. A process for preparing the zinc chloride double salt of Methylene Blue comprising:
 (a) preparing a solution of Methylene Blue as described in Claim 1,
 (b) clarifying the solution and adjusting the pH of the clarified solution to about 2-3,
 (c) adding thereto about 0.5-1.0 mole of zinc chloride per mole of N,N-dimethyl-p-phenylenediamine used to prepare said Methylene Blue, and
 (d) recovering the zinc chloride double salt of Methylene Blue therefrom.

5. The process according to claim 4 wherein
 (a) said clarified solution of Methylene Blue is prepared at about 80°-100° C.,
 (b) the pH of said clarified solution is adjusted to about 2.5 with hydrochloric acid,
 (c) about 0.7-0.9 mole of zinc chloride is added thereto per mole of N,N-dimethyl-p-phenylenediamine used to prepare said Methylene Blue, and
 (d) said zinc chloride double salt of Methylene Blue is recovered therefrom after salting it out from solution.

6. The process according to claim 5 wherein said zinc chloride double salt is salted out by adding sodium chloride thereto.

* * * * *